of Patent: Jul. 14, 1987

United States Patent [19]
Goodall et al.

[11] Patent Number: 4,680,168
[45] Date of Patent: Jul. 14, 1987

[54] EXTRACTION OF GROUP 8 METALS FROM ORGANIC SOLUTIONS

[75] Inventors: Brian L. Goodall; Paulus A. M. Grothenhuis, both of Amsterdam, Netherlands

[73] Assignee: Shell Oil Company, Houston, Tex.

[21] Appl. No.: 872,569

[22] Filed: Jun. 10, 1986

[30] Foreign Application Priority Data

Jun. 20, 1985 [GB] United Kingdom ............... 8515656

[51] Int. Cl.$^4$ ............................................. C01G 55/00
[52] U.S. Cl. .................................... 423/22; 423/139; 423/DIG. 14; 75/97 A; 75/101 BE; 75/108; 75/121; 210/663; 210/685; 502/22; 502/29; 568/454
[58] Field of Search ...................... 568/454, 900, 909; 423/22, 139, DIG. 14; 210/685, 663, 700, 669, 666; 502/152, 22, 29; 75/108, 121, 101 BE, 97 A

[56] References Cited

U.S. PATENT DOCUMENTS

| | | | |
|---|---|---|---|
| 3,882,018 | 5/1975 | Depree | 423/DIG. 14 |
| 3,920,449 | 11/1975 | Onoda et al. | 423/22 |
| 3,966,595 | 6/1976 | Gosser | 502/152 |
| 4,390,473 | 6/1983 | Cooper | 423/22 |
| 4,434,240 | 2/1984 | Pugach | 423/22 |
| 4,496,768 | 1/1985 | Dennis et al. | 568/900 |
| 4,523,036 | 6/1985 | Cornils et al. | 568/909 |
| 4,605,541 | 8/1986 | Pugach | 423/22 |

*Primary Examiner*—John Doll
*Assistant Examiner*—Robert L. Stoll

[57] ABSTRACT

Metals of Group 8 are recovered from an organic medium by liquid-liquid extraction into an aqueous phase in the presence of a water-soluble cyclic phosphite, forming an aqueous extract phase containing the metals in complex combination with the cyclic phosphite.

20 Claims, No Drawings

EXTRACTION OF GROUP 8 METALS FROM ORGANIC SOLUTIONS

FIELD OF THE INVENTION

The invention relates to a process for the extraction of one or more metals of Group 8 of the Periodic Table of the Elements from an organic medium.

BACKGROUND OF THE INVENTION

An organic medium containing one or more metals of Group 8 may be obtained after chemical reactions in which a catalyst bearing such metal(s) is employed.

It is a drawback of the known methods for recovering such metals from organic reaction mixtures that their recovery is incomplete or laborious, particularly if the concentration of such metals in the mixtures is low.

It is an object of the present invention to separate said metals in a highly efficient manner from an organic medium.

In certain important aspects, the present invention accomplishes such separation by a process in which the metal compounds are extracted from the organic medium using an aqueous extractant phase containing a certain cyclic phosphite compound. Prior art relevant to such a process includes U.S. Pat. No. 4,496,768 which describes a process for the production of aldehydes by hydroformylation of alpha-olefins using a complex catalyst of rhodium with cyclic phosphites. The product aldehyde of this prior art hydroformylation process is separated from the rhodium/phosphite catalyst by distillation. British patent specification No. 889,338 describes the preparation of cyclic phosphites from triphenyl phosphites and pentaerythritol and states that the cyclic phosphite products are soluble in water. U.S. Pat. No. 4,523,036 and U.S. Pat. No. Re. 31,812 disclose hydroformylation processes carried out in the presence of water and water-soluble complexes of rhodium with certain cyclic phosphines. Products are recovered by phase separating the organic product from the aqueous solution of the rhodium/phosphine complex.

SUMMARY OF THE INVENTION

The present invention provides a process for the extraction of one or more metals of Group 8 of the Periodic Table of the Elements from an organic medium, in which process the organic medium is contacted with an aqueous phase in the presence of a cyclic phosphite having a bridgehead phosphorus atom linked to three oxygen atoms at least two of which form together with the bridgehead phosphorus atom part of a ring, said cyclic phosphite having a hydroxymethyl group linked to a ring carbon atom, one or more of the hydrogen atoms in the cyclic phosphite optionally being substituted, so as to obtain an aqueous extract phase containing at least a portion of said metals.

It has been found that highly efficient extractions are possible when such an extraction is carried out with a cyclic phosphite as defined hereinbefore. Usually, no metal can be detected in the organic raffinate phase which remains after contacting the organic medium with the aqueous phase.

DESCRIPTION OF THE PREFERRED EMBODIMENTS

The compounds of metals of Group 8 which can be extracted by means of the process according to the present invention are those of iron, cobalt and nickel and, which are preferred, the noble metals, viz. ruthenium, rhodium, palladium, osmium, iridium and platinum. Very good results have been obtained with the extraction of rhodium and palladium compounds.

Any cyclic phosphite of the type defined hereinbefore may be used, provided it is more readily soluble in water than in the organic medium at the temperature at which the extraction is carried out. According to a preferred embodiment of the present invention the cyclic phosphite is a bicyclic phosphite having the general formula

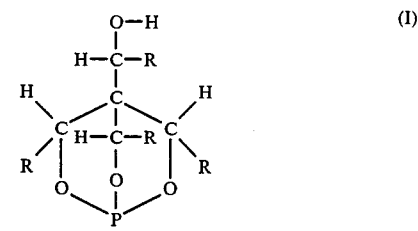

in which each R individually represents a hydrogen atom or an alkyl group having not more than 3 carbon atoms. Preferably, each R represents a methyl group, or, more preferably, a hydrogen atom. Very good results have been obtained with 4-hydroxymethyl-2,6,7-trioxa-1-phosphabicyclo[2,2,2]octane, this compound and its complexes with said noble metals being highly soluble in water.

According to another preferred embodiment of the present invention the cyclic phosphite is a monocyclic phosphite having the general formula

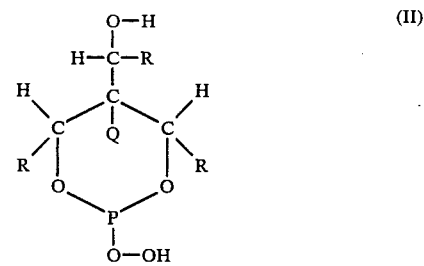

in which each R has the same meaning as in formula (I) and Q represents a hydrogen atom or an alkyl group having not more than three carbon atoms or a group of the general formula

in which R has the same meaning as in formula (I). The group

in the general formula (II) is also meant to include the tautomeric structure

The cyclic phosphites of the general formula (I) and (II) can be prepared by methods known in the art. They may be prepared in situ, for example from a compound of the general formula (I) or (II) in which the hydrogen atom in the H-O-C group is replaced with an atom of an alkali metal or an ammonium group or with a mesylate or p-tosylate group.

The presence of the cyclic phosphite may be brought about in various manners. According to a preferred manner the organic medium is brought into contact with a solution of the cyclic phosphite in a polar solvent, suitably by means of stirring. Stirring is preferably continued until the cyclic phosphite has formed a complex with the metal of Group 8. This usually takes a relatively short time, the metal of Group 8 and the cyclic phosphite being present in one liquid phase, generally after 1 to 150 min. Then, an aqueous phase is added and stirring is continued until equilibrium between the phases has been established. This is generally the case after 1 to 20 min. After phase separation, there are obtained (i) an aqueous extract phase containing at least a portion of the group 8 metal and also containing polar solvent and (ii) an organic raffinate phase.

The presence of the cyclic phosphite may also be brought about by bringing the organic medium containing the Group 8 metal into contact with an aqueous phase containing dissolved cyclic phosphite, suitably by means of stirring. After phase separation, an aqueous extract phase containing at least a portion of the Group 8 metal and an organic raffinate phase are obtained.

According to a further embodiment of the present invention an organic medium containing a Group 8 metal in complex combination with the cyclic phosphite is brought into contact with an aqueous phase, suitably by means of stirring. In this manner, the complex combination is transferred from the organic medium to the aqueous phase.

The starting organic medium may contain very little noble metal, yet extraction efficiency is very high. Favorable concentrations of the noble metal values to be extracted are in the range of from 0.01 to 100 mmol/l, but concentrations below 0.01 mmol/l or 100 mmol/l are not excluded. A favorable volume ratio of the aqueous phase to the organic medium has been found to be in the range of from 0.05 to 2; preferably, this volume ratio is lower than 1. However, volume ratios below 0.05 or above 2 are not excluded.

The metal may be present in any form in the organic medium, for example as a carbonyl compound or as a complex of such a carbonyl with other molecules. Reference herein to metals present in the organic medium is intended to encompass metals present in solution in any form.

Any organic medium containing one or more metals of Group 8 of the Periodic Table of the Elements may be used in the process according to the present invention, provided that upon contacting this medium with the aqueous phase an aqueous extract phase and an organic raffinate phase are formed. According to a preferred embodiment of the present invention the organic medium contains rhodium in complex combination with a compound of trivalent phosphorus, which rhodium has been used as a catalyst compound for the preparation of aldehydes by hydroformylation of an ethylenically unsaturated compound with carbon monoxide and hydrogen in the presence of a solvent for the complex combination. Hydroformylation is a known reaction by which an ethylenically unsaturated compound is reacted with hydrogen and carbon monoxide in the presence of a hydroformylation catalyst—in this case a rhodium complex—to form an aldehyde having one more carbon atom than the starting ethylenically unsaturated compound. This preferred embodiment has the advantage that no rhodium is lost in metallic form and that no shifting of carbon-carbon double bonds takes place in unreacted ethylenically unsaturated compound present in the organic medium. Such shifting of carbon-carbon double bonds and loss of rhodium often takes place when a reaction mixture obtained by hydroformylation is separated in a known manner by means of distillation to isolate the aldehyde in vaporous form and the complex rhodium catalyst in a liquid residue because this distillation may require relatively high temperatures, depending on the prevailing vapor pressure of the aldehyde.

Hydroformylation may be carried out using rhodium in complex combination with the cyclic phosphite described hereinbefore; during such hydroformylation very little shifting of carbon-carbon double bonds has been observed. Alternatively, hydroformylation may be carried out using rhodium in complex combination with a compound of trivalent phosphorus other than the cyclic phosphite, preferably a phosphine. It has, surprisingly, been found that, even in the presence of a large excess of phosphine, this invention is very effective for extracting rhodium from the organic medium. Examples of compounds of trivalent phosphorus are triarylphosphines and triaryl phosphites or mixed aryl aryloxy or mixed aryl alkoxy phosphines and phosphites. The aryl group may be, for example, a phenyl or naphthyl group and may be substituted with, for example, an alkyl group having up to 20 carbon atoms. Examples of suitable compounds are triphenylphosphine, triphenyl phosphite, tri-p-tolylphosphine, tri-p-tolyl phosphite, tri-alpha-naphthylphosphine, tri-alpha-naphtyl phosphite, tri-p-biphenyl phosphite, tri-p-biphenylphosphine, tri-o-chlorophenyl phosphite and tri-o-chlorophenylphosphine. Examples of other ligands suitable for use in combination with rhodium to catalyze hydroformylation reactions are those represented by formula (III)

   (III)

wherein R represents a branched alkyl group or a cycloalkyl group, n represents an integer of 1 or 2 and Ph represents phenyl. The use of such ligands is described in European Patent Application No. 0028378. Other examples of suitable ligands are triarylphosphines which have an electron-withdrawing substituent on an aryl ring; such ligands are described in European Patent Application No. 0102341.

The ethylenically unsaturated compound subjected to hydroformylation may have a carbon-carbon double bond at an alpha- or a non-alpha-position in the molecule, the former possibility being preferred, the reaction rates being considerably higher. Alpha-olefins are usually converted into a mixture of primary and secondary aldehydes, the primary aldehydes being usually the most desirable. Usually, 70% or more of the mixture of aldehydes prepared from alpha-olefins consists of the primary aldehydes.

The said preparation of aldehydes is generally applicable to any aliphatic or cycloaliphatic compound having at least one carbon-carbon double bond. Thus, it is applicable to olefins having, for example, 2 to 30 carbon atoms per molecule, for example, ethylene, propylene, butylene, cyclohexene, 1-octene, 1-dodecene, 1-octadecene and dihydronaphthalene. Suitable hydrocarbons include both branched and straight chain, as well as cyclic compounds having one or more carbon-carbon double bonds. These sites may be conjugated, as in 1,3-butadiene, or non-conjugated, as in 1,5-hexadiene or 1,5-bicyclo[2,2,1]heptadiene. In the case of polyolefins, it is possible to hydroformylate only one of the olefinic sites or several or all of these sites.

Olefinic hydrocarbon fractions, such as, for example, polymeric olefinic fractions and cracked wax fractions containing substantial proportions of non-alpha olefins may be hydroformylates. Such suitable feeds include, for example, $C_7$, $C_8$, $C_9$, $C_{10}$ and higher olefinic fractions as well as olefinic hydrocarbon fractions of wider boiling ranges such as $C_{7-9}$, $C_{10-13}$ and $C_{14-17}$ olefinic hydrocarbon fractions.

Other examples of ethylenically unsaturated compounds which may be hydroformylated are unsaturated alcohols, unsaturated aldehydes and unsaturated acids, which are converted into the corresponding alcohols, aldehydes and acids containing a formyl group in one of the carbon atoms previously involved in the carbon-carbon double bond of the starting ethylenically unsaturated compound.

Generally, hydroformylation is carried out under rather mild conditions, preferably at a temperature in the range of from 40° C. to 160° C. and a total pressure in the range of from 1 to 50 bar. Generally, a molar ratio of ligand of formula (III) to rhodium in the range of from 0.5 to 5000 is used; usually, this ratio is at least 3.

The amount of rhodium may vary within wide ranges; generally a molar ratio of ethylenically unsaturated compound to rhodium in the range of from 150,000 to 10 and more often from 100,000 to 1000 is used.

The rhodium may be introduced into the complex combination in any desired manner, for example, as 1,5-cyclooctadiene-rhodium(I) acetate, 1,5-cyclooctadiene-rhodium(I) acetylacetonate, rhodium acetate, dirhodium octacarbonyl, finely divided rhodium metal, rhodium nitrate, tetrarhodium dodecarbonyl or hexarhodium hexadeca-carbonyl.

Generally, a molar ratio of hydrogen to carbon monoxide in the range of from 0.5 to 12 is used in conducting the hydroformylation.

The process according to the present invention results—if applied to extraction of rhodium used as a catalyst in a hydroformylation reaction—upon phase separation, in an organic raffinate phase containing aldehyde, any ligand other than the cyclic phosphite and, usually, unreacted ethylenically unsaturated compound, and an aqueous extract phase containing rhodium in complex combination with the cyclic phosphite. Suitably, the aqueous extract phase is separated by means of distillation into a distillate fraction containing water and a residual fraction containing rhodium in complex combination with the cyclic phosphite. Distilling off water from the aqueous phase may be facilitated by the presence of a compound forming an azeotropic mixture with water, for example, of cyclohexane. As such a distillation can be carried out at relatively low temperature, and no metallic rhodium is formed. The solvent for the rhodium complex may remain in the residual fraction or may be distilled off, depending on the boiling point thereof. If desired, the rhodium in complex combination with the cyclic phosphite present in the residual fraction may be reused for hydroformylation. Alternatively, it may be converted into a hydroformylation catalyst comprising rhodium in complex combination with a phosphine or with a phosphite other than the said cyclic phosphite; this may be carried out by, for example, burning the rhodium-cyclic phosphite complex with formation of rhodium dioxide, which, in turn, is converted in a known manner into a hydroformylation catalyst.

Suitable solvents for the complex of rhodium with the cyclic phosphite are polar and more readily soluble in water than in the organic reaction mixture. The aqueous extract phase then, will contain the polar solvent as well. Examples of suitable solvents are carboxamides, for example, dimethylformamide, N,N-dimethylacetamide and N-methylpyrrolidone, sulphoxides, for example, dimethyl sulphoxide and diethyl sulphoxide, tetrahydrothiophene, 1,1-dioxide (also referred to as "sulfolane") and derivatives thereof (for example 3-methylsulfolane).

Other examples of suitable solvents are alcohols, such as methanol, ethanol and 2-propanol, esters, such as ethyl acetate, ketones, such as acetone and methyl isobutyl ketone and ethers, such as 1,4-dioxane, tetrahydrofuran and anisole.

The invention is further illustrated by means of the following Examples. The phosphite used in the Examples was 4-hydroxymethyl-2,6,7-trioxa-1-phosphabicyclo[2,2,2]octane, indicated in the Examples as "POP".

EXAMPLES 1 AND 2

A (300-ml) stainless steel autoclave equipped with a mechanical stirrer, a gas inlet tube, a thermocouple pipe and a pressure indicator was charged with 1-decene (0.4 mol), ethanol (50 ml), 1,5-cyclooctadiene-rhodium(I) acetate (0.08 mmol) and POP (1.055 mmol), the molar ratio POP to rhodium being 13.2. The 1-decene had been purified by means of an elution-over basic aluminum oxide. The autoclave was flushed with an equimolar mixture of hydrogen and carbon monoxide and then pressurized to 10 bar with this mixture. The reaction mixture was heated up to 90° C. while maintaining the pressure at 10 bar. After a total reaction time of 23 hours the mixture was allowed to cool to ambient temperature. The autoclave was depressurized and the reaction mixture was pumped under air into a separatory funnel for extraction with water (once, 25 ml, the volume ratio of the aqueous phase to the reaction mixture being 1:5). After phase separation no rhodium could be detected in the organic phase, the rhodium content therefore being less than 1 part per million by weight. The organic phase contained the aldehyde product, unreacted 1-decene and non-alpha decenes. All of the non-alpha decenes had been formed in the autoclave, no formation thereof being observed during the extraction with water. From the aqueous layer the solvents (ethanol and water) were removed by means of a simple flash over a rotavapour, leaving behind a solid complex containing rhodium and POP. This solid complex was dissolved in fresh ethanol and re-used as catalyst in Example 2 in the same manner as in Example 1. The results are stated in Table I. The percentage of the starting 1-decene that has been converted into non-alpha decenes is presented under the heading "non-alpha decenes" and the linearity is defined as the percentage of n-undecanal in the mixture of aldehydes formed.

EXAMPLE 3

The autoclave as used in Example 1 was charged with 1-decene (0.4 mol), dimethylacetamide, (50 ml), 1,5-cyclooctadiene-rhodium(I) acetylacetonate (0.08 mmol) and POP (1.03 mmol), the molar ratio of POP to rhodium being 12.9. Then, the procedure of Example 1 was followed. After a total reaction time of 5 hours the mixture was allowed to cool to ambient temperature. The autoclave was depressurized and the reaction mixture was pumped under air into a separatory funnel for extraction with water (once, 10 ml, the volume ratio of the aqueous phase to the reaction mixture being 1:12.5). After phase separation no rhodium could be detected in the organic phase, the content thereof being less than 1 part per million by weight. The organic phase contained the aldehyde product, unreacted 1-decene and non-alpha decenes. All of the non-alpha decenes had been formed in the autoclave, no formation thereof being observed during the extraction with water. From the aqueous layer water was removed azeotropically with cyclohexane at a pressure of 21 kPa and a maximum temperature of 80° C., leaving behind a solution of a complex containing rhodium and POP in dimethylacetamide. The results are presented in Table I.

TABLE I

| Example | Solvent | Time, h | Conversion, % | Non-alpha decenes, % | Linearity, % |
|---|---|---|---|---|---|
| 1 | ethanol | 23 | 94.6 | 4 | 75 |
| 2 | " | 9 | 95.6 | 8 | 70 |
| 3 | dimethylacetamide | 5 | 92.4 | 6 | 71 |
| 4 | dimethylacetamide | 4 | 97.4 | 5.5 | 71 |
| 5 | dimethylacetamide | 4 | 98.0 | 6 | 70 |
| 6 | dimethylacetamide | 4 | 98.7 | 6 | 70 |
| 7 | dimethylacetamide | 4 | 97.5 | 10 | 72 |

EXAMPLE 4

The solution of the complex obtained in Example 3 was re-used as catalyst in the same manner as in Example 3. The results are stated in Table I.

EXAMPLE 5

The solution of the complex obtained in Example 4 was re-used as catalyst in the same manner as in Example 4. The results are stated in Table I.

EXAMPLE 6

The solution of the complex obtained in Example 5 was re-used as catalyst in the same manner as in Example 5. The results are stated in Table I.

EXAMPLE 7

Example 3 was repeated using 0.016 instead of 0.08 mmol of 1,5-cyclooctadiene-rhodium(I) acetylacetonate and 0.2 mmol POP instead of 1.03 mmol. The results are presented in Table I.

Comparison of the results obtained in Example 3 with those of Examples 4, 5 and 6 shows that the complex catalyst did not lose activity after recycle, while maintaining a high linearity. These facts confirm that very little rhodium was lost.

EXAMPLE 8

$RhH[CO][P(C_6H_5)_3]_3$ (0.013 mmol) and triphenylphosphine (27.2 mmol), the molar ratio of triphenylphosphine to the rhodium compound being 2000, were dissolved in dimethylacetamide (20 ml). Then, a mixture of 1-decene (30 ml) and toluene (20 ml) was added. To the mixture thus obtained a solution of POP (0.26 mmol, molar ratio POP to Rh being 20) in dimethylacetamide (10 ml) was added and the mixture was stirred for 15 min, the concentration of rhodium in the organic phase being 0.16 mmol/l. Subsequently, water (50 ml) was added, the volume ratio aqueous phase to organic phase being 0.6, followed by shaking and allowing to stand in a separating funnel. The lower (aqueous) layer was separated off and distilled to dryness giving a white solid. The organic layer (46 g) was analyzed for rhodium by atomic adsorption spectroscopy.

No rhodium could be observed in the organic layer, which means that the rhodium content thereof was less than 1 part per million by weight (ppm), while a concentration of 28 ppm would be expected if no extraction had taken place.

EXAMPLE 9

An amount of palladium acetylacetonate (0.32 mmol) and of triphenylphosphine (3.24 mmol, the molar ratio of phosphine to palladium compound being 10) were dissolved in toluene (60 g), thus forming a red palladium complex. To the solution POP (1.8 mmol) dissolved in ethanol (40 g) was added, the molar ratio POP to Pd being 5.6, and the mixture was stirred for 30 min, the concentration of palladium in the organic phase being about 2.5 mmol/l. Then, water (20 ml) was added, the volume ratio aqueous phase to organic phase being about 0.2, followed by stirring for 10 min. After phase separation the aqueous layer contained 97% of the starting amount of palladium and the organic layer 3%. A second water wash (20 ml) was sufficient for quantitative removal of palladium from the organic phase.

EXAMPLE 10

1-Decene was hydroformylated in the presence of $RhH[CO][P(C_6H_5)_3]_3$ followed by distillation of the reaction mixture, yielding a residue of heavy ends containing a complex (0.037 mmol) of rhodium with triphenylphosphine and 37 mmol of free triphenylphosphine, the molar ratio of triphenylphosphine to rhodium complex being 1000. To this residue a solution of POP (1.2 mmol, molar ratio POP to Rh being 32) in dimethylacetamide (50 ml) was added and the mixture was stirred for 2 hours. Then, water (20 ml) was added and after stirring and phase separation the aqueous and organic layer were analysed, indicating that 95% of the starting amount of rhodium was present in the aqueous phase.

We claim as our invention:

1. A process for the extraction of one or more metals of Group 8 of the Periodic Table of the Elements from an organic medium, which comprises (a) contacting the organic medium with an aqueous phase in the presence of a cyclic phosphite of the formula

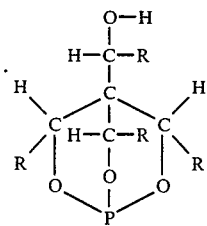

wherein each R individually represents a hydrogen atom or an alkyl group having not more than three carbon atoms, or of the formula

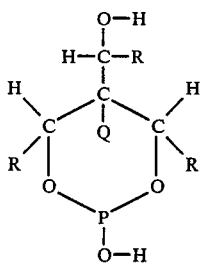

wherein Q represents a hydrogen atom or an alkyl group having not more than three carbon atoms or a group of the formula

and R, in each occurrence, represents a hydrogen atom or an alkyl group having not more than three carbon atoms, to obtain an aqueous extract phase containing at least a portion of said metals and an organic raffinate phase from which said metals have at least in part been extracted, and (b) phase separating the aqueous extract phase from the organic raffinate phase.

2. The process as claimed in claim 1, in which the cyclic phosphite is a bicyclic phosphite having the general formula

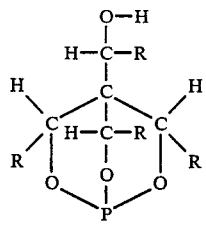 (I)

in which each R individually represents a hydrogen atom or an alkyl group having not more than 3 carbon atoms.

3. The process as claimed in claim 2, in which the bicyclic phosphite is 4-hydroxymethyl-2,6,7-trioxa-1-phosphabicyclo[2,2,2]octane.

4. The process as claimed in claim 1, in which the cyclic phosphite is a monocyclic phosphite having the general formula

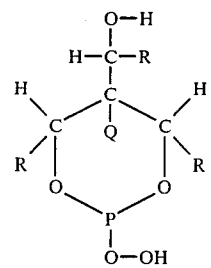 (II)

in which Q represents a hydrogen atom or an alkyl group having not more than three carbon atoms or a group of the general formula

and R, in each occurrence, represents a hydrogen atom or an alkyl group having not more than 3 carbon atoms.

5. The process as claimed in claim 2, in which a volume ratio of the aqueous phase to the organic medium in the range of from 0.05 to 2 is used.

6. The process as claimed in claim 2, in which the metal of Group 8 is a noble metal.

7. The process as claimed in claim 6, in which the noble metal is palladium.

8. The process as claimed in claim 6, in which the noble metal is rhodium.

9. The process as claimed in claim 8, in which the organic medium contains rhodium in complex combination with a compound of trivalent phosphorus, which rhodium has been used as a catalyst component for the preparation of aldehydes by hydroformylation of an ethylenically unsaturated compound with carbon monoxide and hydrogen in the presence of a solvent for the complex combination.

10. The process as claimed in claim 9, in which the rhodium is present in the organic medium in complex combination with the said cyclic phosphite.

11. The process as claimed in claim 9, in which the rhodium is present in the organic medium in complex combination with a compound of trivalent phosphorus other than the cyclic phosphite.

12. The process as claimed in claim 11, in which the compound of trivalent phosphorus is a phosphine.

13. The process as claimed in claim 4, in which a volume ratio of the aqueous phase to the organic medium in the range of from 0.05 to 2 is used.

14. The process as claimed in claim 4, in which the metal of Group 8 is a noble metal.

15. The process as claimed in claim 14, in which the noble metal is palladium.

16. The process as claimed in claim 14, in which the noble metal is rhodium.

17. The process as claimed in claim 16, in which the organic medium contains rhodium in complex combination with a compound of trivalent phosphorus, which rhodium has been used as a catalyst component for the preparation of aldehydes by hydroformylation of an ethylenically unsaturated compound with carbon monoxide and hydrogen in the presence of a solvent for the complex combination.

18. The process as claimed in claim 17, in which the rhodium is present in the organic medium in complex combination with the said cyclic phosphite.

19. The process as claimed in claim 17, in which the rhodium is present in the organic medium in complex combination with a compound of trivalent phosphorus other than the cyclic phosphite.

20. The process as claimed in claim 19, in which the compound of trivalent phosphorus is a phosphine.

* * * * *